United States Patent [19]

Brewer et al.

[11] Patent Number: 5,700,281
[45] Date of Patent: Dec. 23, 1997

[54] STAGE AND STATE MONITORING AUTOMATED EXTERNAL DEFIBRILLATOR

[75] Inventors: James E. Brewer, St. Paul; Kenneth F. Olson, Edina; John F. Stolte, Burnsville; Nora J. Utke, Minneapolis; Gary B. Stendahl, Crystal, all of Minn.

[73] Assignee: SurVivaLink Corporation, Minneapolis, Minn.

[21] Appl. No.: 668,117

[22] Filed: Jun. 17, 1996

Related U.S. Application Data

[63] Continuation-in-part of Ser. No. 658,200, Jun. 4, 1996.
[51] Int. Cl.[6] .............................. A61N 1/39; A61N 1/04; A61N 1/08
[52] U.S. Cl. .............................. 607/5; 607/142; 607/152
[58] Field of Search .............................. 607/5, 8, 142, 607/152

[56] References Cited

U.S. PATENT DOCUMENTS

| 3,886,950 | 6/1975 | Ukkestad et al. | 607/5 |
|---|---|---|---|
| 4,494,552 | 1/1985 | Heath | 128/696 |
| 4,610,254 | 9/1986 | Morgan et al. | 607/6 |
| 4,619,265 | 10/1986 | Morgan et al. | 607/6 |
| 5,014,697 | 5/1991 | Pless et al. | 607/8 |
| 5,097,830 | 3/1992 | Eikefjord et al. | 607/8 |
| 5,402,884 | 4/1995 | Gilman et al. | 206/328 |
| 5,462,157 | 10/1995 | Freeman et al. | 128/640 |
| 5,470,343 | 11/1995 | Fincke et al. | 607/5 |
| 5,496,349 | 3/1996 | Campbell et al. | 607/5 |
| 5,591,213 | 1/1997 | Morgan | 607/5 |
| 5,620,465 | 4/1997 | Olson et al. | 607/5 |

FOREIGN PATENT DOCUMENTS

WO 94/27674  12/1994  WIPO .............................. A61N 1/39

*Primary Examiner*—William E. Kamm
*Assistant Examiner*—Carl H. Layno
*Attorney, Agent, or Firm*—Patterson & Keough, P.A.

[57] ABSTRACT

A circuit detectable arrangement of a plurality of medical electrodes is provided with each electrode having an electrically nonconductive backing layer, a layer of electrically conductive adhesive disposed on the backing layer and a lead wire extending therefrom and electrically connected with the conductive adhesive. More specifically, a first electrode is disposed on an electrically nonconductive liner, a second electrode is disposed on an electrically nonconductive liner, and an electrical connector is provided between the first and second electrodes for electrically completing a circuit connecting the lead wire of the first electrode to the lead wire of the second electrode. Preferably, the backing layers of the first and second electrodes each include a conductor portion, and the electrical connector is connected between the conductor portion of the backing layer of the first electrode and the conductor portion of the backing layer of the second electrode. The electrical connector preferably comprises a strip of flexible and electrically conductive material and may include a nonconductive tear resistant strip. Utilizing the electrode packaging above, the present invention monitors the state of the AED and the stage of a rescue. In particular, at least five stages of a rescue are monitored. These include: 1) rescue initiated; 2) preparing victim; 3) applying electrodes; 4) AED in use; and 5) rescue completed.

31 Claims, 8 Drawing Sheets

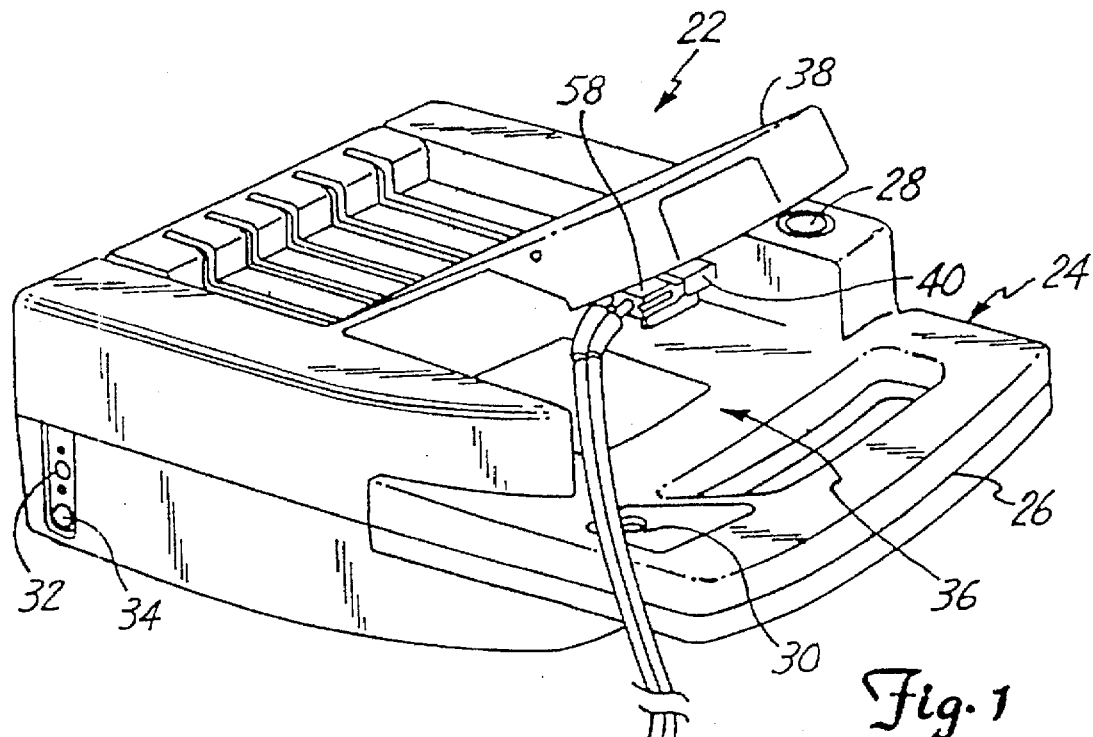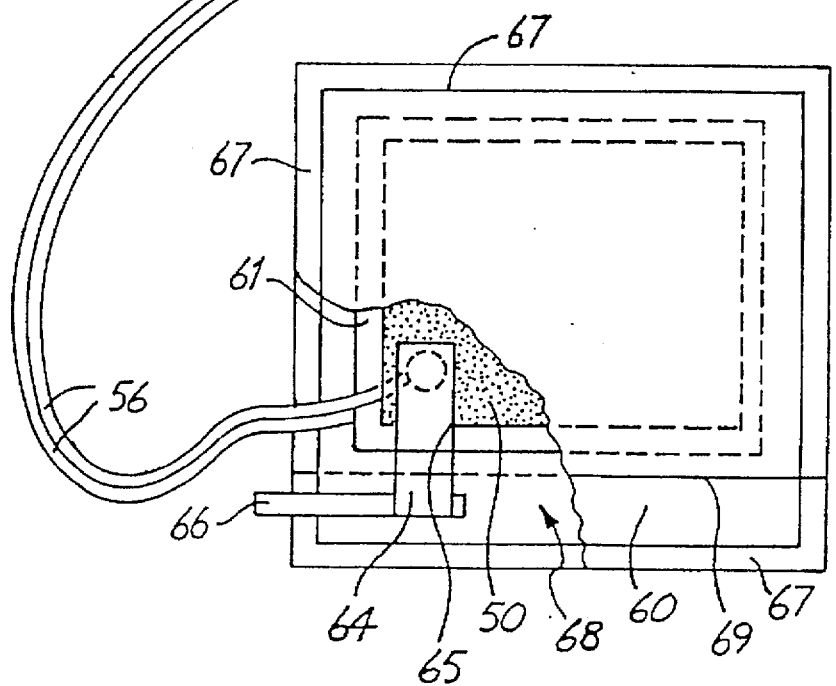
Fig. 1

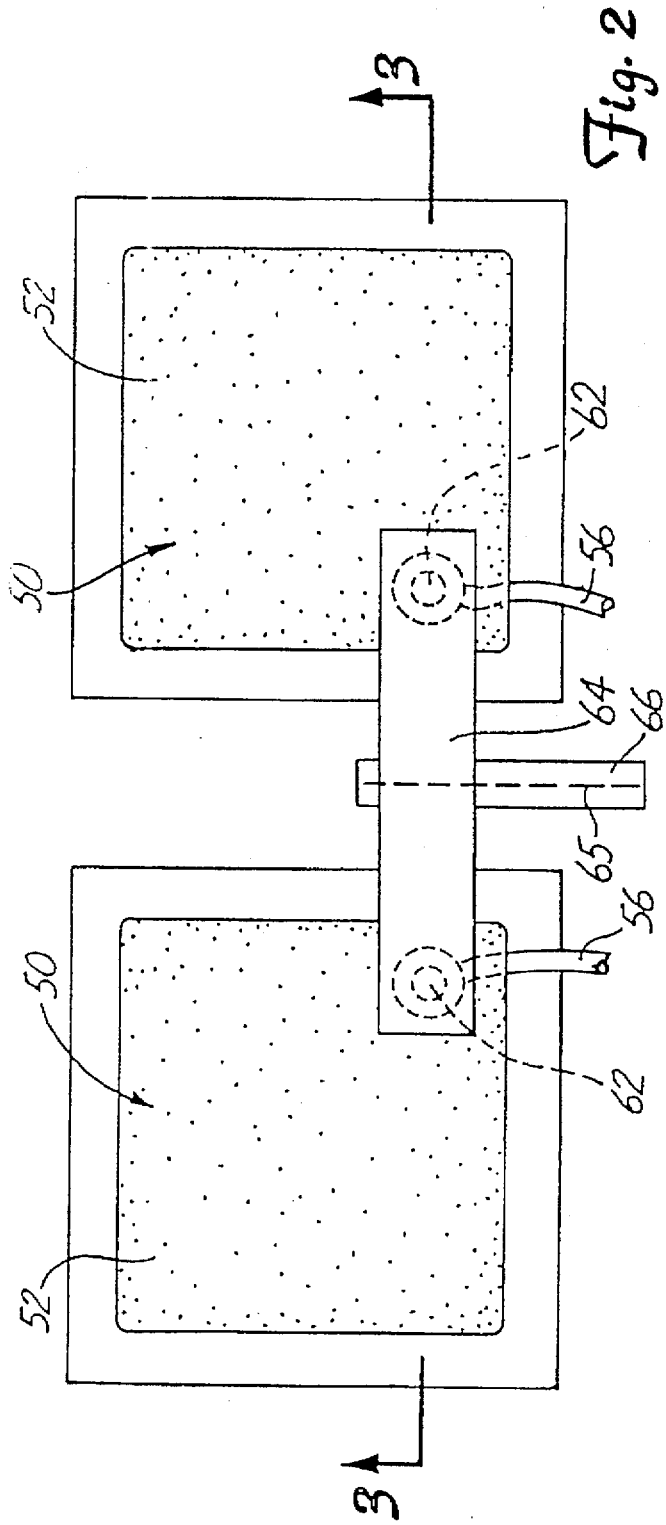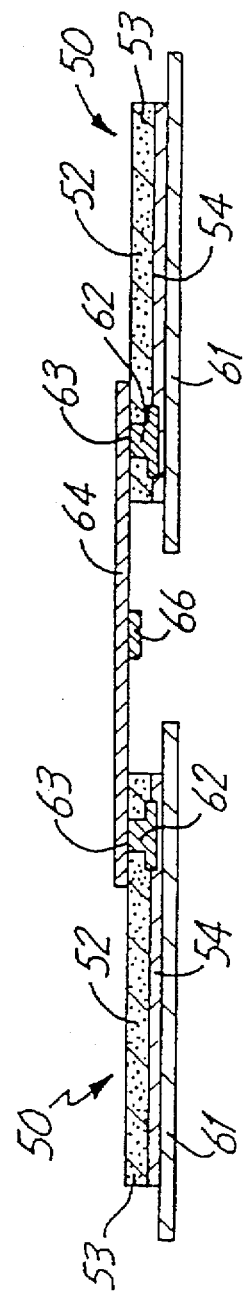

STAGE AND STATE MONITORING AUTOMATED EXTERNAL DEFIBRILLATOR

RELATED APPLICATIONS

The present invention is a continuation-in-part of co-pending U.S. patent application Ser. No. 08/658,200 entitled Circuit Detectable Packaged Medical Electrodes, filed Jun. 4, 1996.

FIELD OF THE INVENTION

The present invention relates to automated external defibrillators (AEDs). In particular, the present invention is an AED capable of monitoring the state of the AED and the stage of a rescue.

BACKGROUND OF THE INVENTION

Electrodes are used with numerous devices in the medical field. One such application is with an automated external defibrillator (AED). AEDs are used by first-responder emergency medical technicians to resuscitate cardiac arrest patients. It is important that AEDs carried by these technicians be continuously operational and ready for use on a moment's notice. To help ensure a high level of confidence that they will be operational when needed, AEDs must be periodically checked and tested by the technicians, and corrective maintenance performed if any faults are identified. AED's functions and components that should be periodically checked and tested, for example, include the charge state of batteries, the presence of electrodes and the ability of the device to charge and deliver defibrillation pulses.

An automated external defibrillator with self-test system has been developed and is disclosed in co-pending U.S. patent application Ser. No. 08/512,441, entitled "Automated External Defibrillator with Self-Test System," which is commonly assigned to the assignee of the subject application, and the entire contents of which are incorporated herein by reference. Disclosed is a defibrillator that includes a digital control system having self-test means for periodically and automatically performing self-tests of one or more defibrillator components. If a malfunctioning component is identified, the self-test means actuates an audible alarm or other maintenance indicator to alert an operator. Specifically tested functions include the presence and interconnection of defibrillator electrodes, battery-charge state, the functionality of the high voltage circuit and the functionality of the digital control system. Some functions are self-tested daily, while others are self-tested weekly.

In order to test the presence and interconnection of defibrillator electrodes, the defibrillator electrodes must be packaged or otherwise arranged in a way to permit the testing. Specifically, it is described in the aforementioned co-pending application Ser. No. 08/512,441 that a pair of electrodes together form a part of an electric circuit through which current is run during the self-test and the impedance measured. A relatively low impedance, (e.g., less than about 10 ohms) indicates the presence of a pair of electrodes. In order for the electrodes to make up and complete an electrical circuit, both electrodes are electrically connected with one another so that a circuit can comprise the electrical lead wires of each electrode. To do this, the electrically conducive adhesive layers of each of the pair of electrodes are affixed in a face-to-face orientation to opposite sides of a release liner within a package. The release liner is perforated with a number of apertures so that the electrodes are electrically coupled to one another within the package. A relatively low resistance electrical circuit is thereby established between the ends of the lead wires.

The above-described system effectively detects the presence of a pair of electrodes as provided in the package. An additional advantage is that the freshness of the packaged electrodes can be determined because the conductive adhesive layers increase in resistance as they dry out over time. However, a problem that the circuit cannot distinguish between is new electrodes and electrodes that have been used or tampered with and subsequently stuck back together, with or without the perforated release liner. Additionally, the circuit cannot determine what stage an ongoing rescue is in.

Medical electrode packaging is also described in U.S. Pat. No. 5,402,884 to Gilman, et al., which is assigned to the assignee of the present invention. In one embodiment, a sealed package is disclosed containing a pair of medical electrodes with conductive adhesive layers facing one another and separated from one another by a resistive layer. A circuit can be completed through the lead wires of each electrode, through the conductive adhesive of each electrode, and through the resistive layer. Again, by monitoring resistance through the circuit, the presence of the electrodes can be detected. Also disclosed in the Gilman, et al. patent are a number of other packages for single medical electrodes. In each case, at least one conductor is provided through the package so that a circuit can be completed through the package and a portion of the conductive adhesive layer of the one electrode. While these packages are useful for their intended purpose, further information about the AED and the rescue is desirable.

SUMMARY OF THE INVENTION

In accordance with the present invention, an automated external defibrillator (AED) having a circuit detectable arrangement of medical electrodes and a package thereof is provided that overcome the disadvantages and shortcomings of the prior art. Specifically, the AED of the present invention can detect the presence or absence of a fresh package of electrodes and can also detect the state of the AED and the stage of an ongoing rescue.

In accordance with one aspect of the present invention, a circuit detectable arrangement of a plurality of medical electrodes is provided with each electrode having an electrically nonconductive backing layer, a layer of electrically conductive adhesive disposed on the backing layer and a lead wire extending therefrom and electrically connected with the conductive adhesive. More specifically, a first electrode is disposed on an electrically nonconductive liner, a second electrode is disposed on an electrically nonconductive liner, and an electrical connector is provided between the first and second electrodes for electrically completing a circuit connecting the lead wire of the first electrode to the lead wire of the second electrode. Preferably, the backing layers of the first and second electrodes each include a conductor portion, and the electrical connector is connected between the conductor portion of the backing layer of the first electrode and the conductor portion of the backing layer of the second electrode. The electrical connector preferably comprises a strip of flexible and electrically conductive material and may include a nonconductive tear resistant strip.

Utilizing the electrode packaging above, the present invention can monitor the state of the AED and the stage of a rescue. In particular, at least five stages of a rescue can be monitored. These include: 1) rescue initiated; 2) preparing victim; 3) applying electrodes; 4) AED in use; and 5) rescue completed.

BRIEF DESCRIPTION OF THE DRAWINGS

FIG. 1 is a perspective view of an automated external defibrillator (AED) with a pair of electrodes according to the present invention attached thereto.

FIG. 2 is a detailed plan view of unpackaged electrodes positioned on release liners.

FIG. 3 is a cross-sectional view through the pair of electrodes of FIG. 2 taken along line 3—3.

DETAILED DESCRIPTION OF THE PREFERRED EMBODIMENTS

Figure 4:
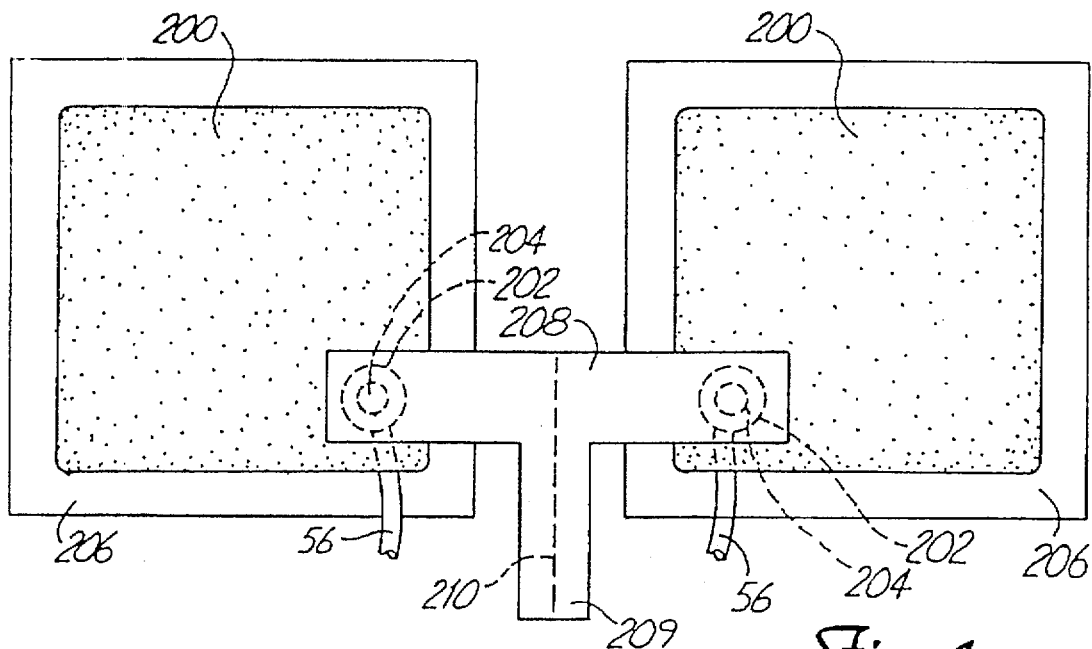
FIG. 4 is detailed plan view of a second embodiment of unpackaged electrodes.

The present invention is an automated external defibrillator (AED) having a circuit detectable arrangement of medical electrodes and a package therefore.

FIG. 1 illustrates a pair of electrodes 50 connected to an AED 22. As can be seen in FIG. 1, defibrillator 22 includes a plastic case 24 with a carrying handle 26 on the top portion. An illuminable rescue switch 28, visual maintenance indicator 30, data communication port 32 and charging port 34 are located on the outside of case 24 for easy access by an operator. Case 24 also includes an electrode compartment 36 which is enclosed by a lid 38 which is mounted to the case by hinges (not shown). Finger-receiving recess 31 in lid 28 is grasped to open the lid and access the electrode compartment 36. An electrode connector 40, speaker 41 and diagnostic display panel 36 are located on case 12 within electrode compartment 26. Diagnostic display panel 37 includes Resume switch 48 and resume indicator light 49.

Defibrillator electrodes 50, as illustrated in FIGS. 1 and 2, each include a polymer backing layer 52, and a patient-engaging layer 54 of conductive adhesive which overlays the backing layer. In one embodiment of the electrodes, backing layer 52 is a flexible polymeric foam. Conductive adhesives for electrode use are well-known and commercially available, such as Ludlou Technical Products' conductive hydrogel. A current-dispersing flexible conductive sheet (not seen in FIG. 1) is preferably located between backing layer 52 and patient-engaging layer 54 so as to disperse current over conductive adhesive layer 54. The conductive sheet need not be the same size as the electrode and is preferably a homogeneous, solid, thinly deposited metallic substance, or a conductive ink. Meshes or patterns of conductive adhesives or inks may be used.

Insulated lead wires 56 extend from each electrode 50, and have a first end connected within each electrode 50 to its conductive sheet and a second end connected to a connector 58. Connector 58 is configured to releasably mate with electrode connector 40 in electrode compartment 36, as illustrated. Electrodes 50 are sealed within a polymer or polymer-metal laminate package 60. Lead wires 56 and connector 58 extend from package 60.

A first embodiment of a pair of electrodes 50 to be provided within package 60 is shown in FIGS. 2 and 3. The package design of FIG. 1 illustrates electrodes 50 folded against one another and provided within package 60. As shown in FIG. 2, each electrode 50 includes backing layer 52, patient-engaging layer 54 of conductive adhesive, a conductive sheet 53 (illustrated in FIG. 3) between layers 52 and 54, and a liner 61. Liner 61 can comprise any conventional lining material such as plastic sheeting or treated papers. Both electrodes 50 may be provided together on a single liner sheet; however, for reasons set out below, other compensations would be necessary. It should be noted that liner 61 may be comprised of a solid piece of material or have a plurality of perforations formed therein.

A lead wire 56 connects with each electrode 50. Specifically, lead wire 56 extends partially within each electrode 50, preferably between backing layer 52 and conductive adhesive layer 54. A terminal 62 is provided at the end of lead wire 56 within each electrode 50 for preferably connecting the conductive wire of lead wire 56 to conductive sheet 53. Otherwise, terminal 62 may directly conduct current to conductive adhesive layer 54.

In accordance with the present invention, each terminal 62 preferably extends through backing layer 52 so as to provide a conductor 63 at the surface of backing layer 52. Conductors 63 are connected together electrically by a flexible conductive connector 64. Conductive connector 64 preferably comprises a metal foil or a fine wire which can be folded for packaging and easily torn or broken, the reasons for which will be evident from the description below. Moreover, connector 64 can be conventionally electrically connected to conductors 63 by conductive adhesive, heat bonding solder, or the like. Preferably, conductors 63 and conductive connector 64 are positioned and arranged, such as that illustrated in FIG. 2, so that when electrodes 50 are to be packaged within package 60, they can be folded against one another by a fold line 65 bisecting conductive connector 64. By this arrangement, an electrical circuit can be completed between lead wires 56 through terminals 62, conductors 63, and connecting conductor 64. Also preferably provided, is a strip of tear resistant material 66 that is more preferably provided at about the midpoint of conductor connector 64 and which extends transverse to the direction of connector 64. Tear resistance strip 66 may comprise a plastic, paper or other nonconductive material which is tear resistant as compared to the material of conductive connector 64.

Referring back to FIG. 1, electrodes 50 are folded toward one another along fold line 65 and positioned within a pouch type package 60 that can be conventionally made either of two sheets connected together or a single sheet folded and sealed at its edges 67. One of sealed edges 67 accommodates the passage of lead wires 56 from package 60 by forming a small opening through the edge. Preferably also, edge 67 also accommodates passage of a portion of tear resistant strip 66 from the interior of package 60 to the outside of package 60. A tear line 69 is also provided along package 60 dividing interior portion 68 of package 60 from the rest of the inside of the package that is inhabited by the folded pair of electrodes. Tear line 69 may be facilitated by a line of weakening or other means for controlling package opening along tear line 69. Conductive connector 64 preferably extends within package 60 sufficiently from each electrode 50 into package interior portion 68 so that tear resistant strip 68 also lies completely within interior portion 68.

To open package 60, a user is instructed to tear the package along tear line 69. The portion of tear resistant strip 66 extending from package 60 can be used for gabbing by the user to open the package. Otherwise, the user would simply rip along tear line 69. In tearing open package 60 along tear line 69, conductive connector 64 will be likewise torn or broken. Thus, by opening package 60, the circuit between lead wires 56 of electrodes 50 within package 60 will be broken. The provision of tear resistant strip 66 not only provides an extension for grabbing to begin opening package 60, it also ensures that conductive connector 64 will be broken during a tearing operation. As a result of this construction, the presence of an unbroken conductive connector 64 and the subsequent breaking thereof during usage of electrodes 50 can be automatically detected for determining the presence of fresh electrodes 50.

Figure 5:
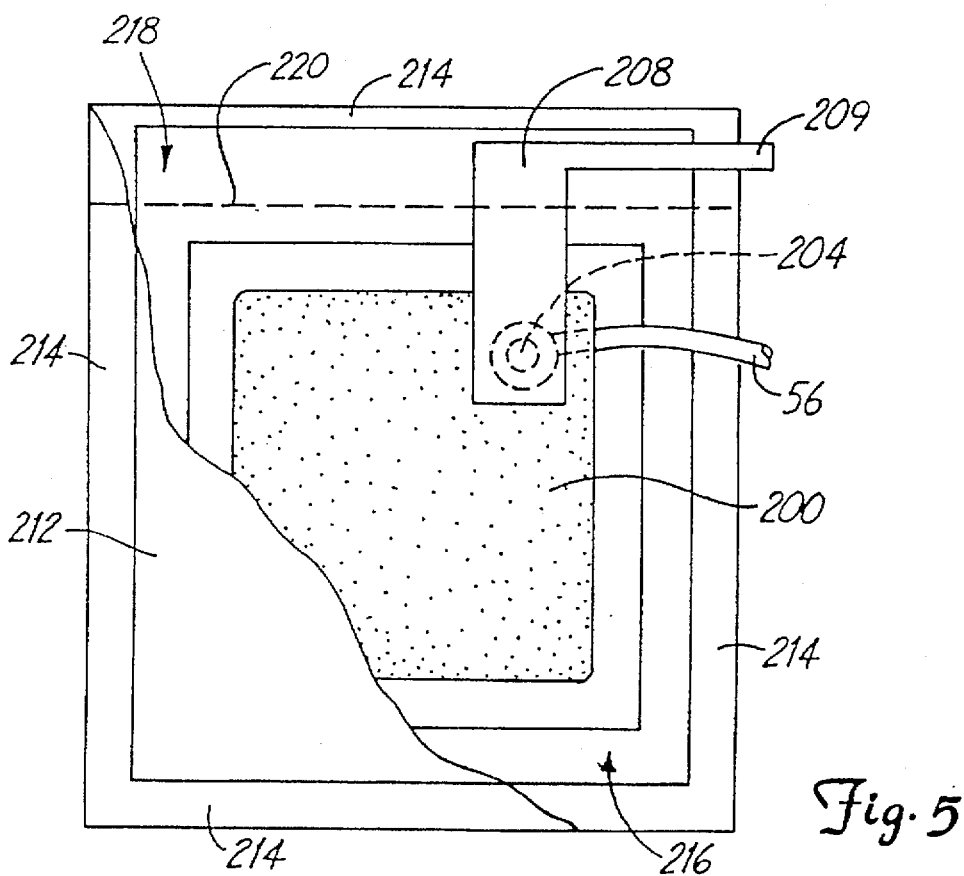
FIG. 5 is a plan view of the electrodes of FIG. 4 folded one on top of the other and provided within a package shown partially broken away.

A second embodiment of a pair of electrodes 200 is illustrated in FIGS. 4 and 5. Specifically, the construction of each electrode 200 is preferably the same as that described above including a backing layer, a patient-engaging conductive adhesive layer, and a current dispersing flexible conducting sheet therebetween. Likewise, lead wires 56 extend partially within electrodes 200 between the backing layer and the conductive adhesive layer of each electrode 200 and are preferably connected with the conductive sheets at terminals 202. Terminals 202 similarly provide conductors 204 at the surface of the backing layers of each electrode 200. Electrodes 200 are each provided on separate liners 206. As with the previous embodiment, a single liner could be used. A pair of electrodes 200 are connected together by a conductive connector 208 specifically connected from one conductor 204 of one electrode 200 to conductor 204 of another electrode 200. Again, conductors 204 can be conventionally connected to conductive connector 208 by conductive adhesive, heat bonding, solder or the like. Conductive connector 208 preferably comprises a thin metal foil. Moreover, in accordance with this embodiment, conductor connector 208 includes an extension portion 209 that is preferably integrally formed with conductive connector 208. Portion 209 extends transversely from conductive connector 208 preferably at about center fold line 210, and extends substantially further than the edge of liners 206.

In order to provide electrodes 200 within a package 212, shown in FIG. 5, the construction and arrangement shown in FIG. 4 is folded substantially on fold line 210 so that electrodes 200 are positioned back to back with liners 206 against one another. Package 212 can be a conventional construction pouch having edge seals 214 around its periphery. Electrodes 200 are received within an electrode interior portion 216 which is divided from an interior portion 218 by a tear line 220. As above, lead wires 56 are accommodated through one of edge seals 214. Likewise, portion 209 of conductive connector 208 preferably extends sufficiently that it extends through the same edge seal to facilitate opening of the package. Conductive connector 208 preferably extends within the package sufficiently from each electrode 200 into package interior portion 218 so that portion 209 of conductive connector 208 lies within interior package portion 218.

Then, to open package 212, a user would simply grasp the package at or near extension portion 209 and tear the package open along tear line 220. Extension portion 209 ensures that tearing along tear line 220 by grasping extension point 209 will tear through conductive connector 208 and break the circuit between lead wires 56. As above, the function of making and generating the circuit completed by conductive connection 208 and terminals 202 between lead wires 56 can be monitored by defibrillator 22, as described generally below, for determining the presence of fresh electrodes 200.

Figure 6:
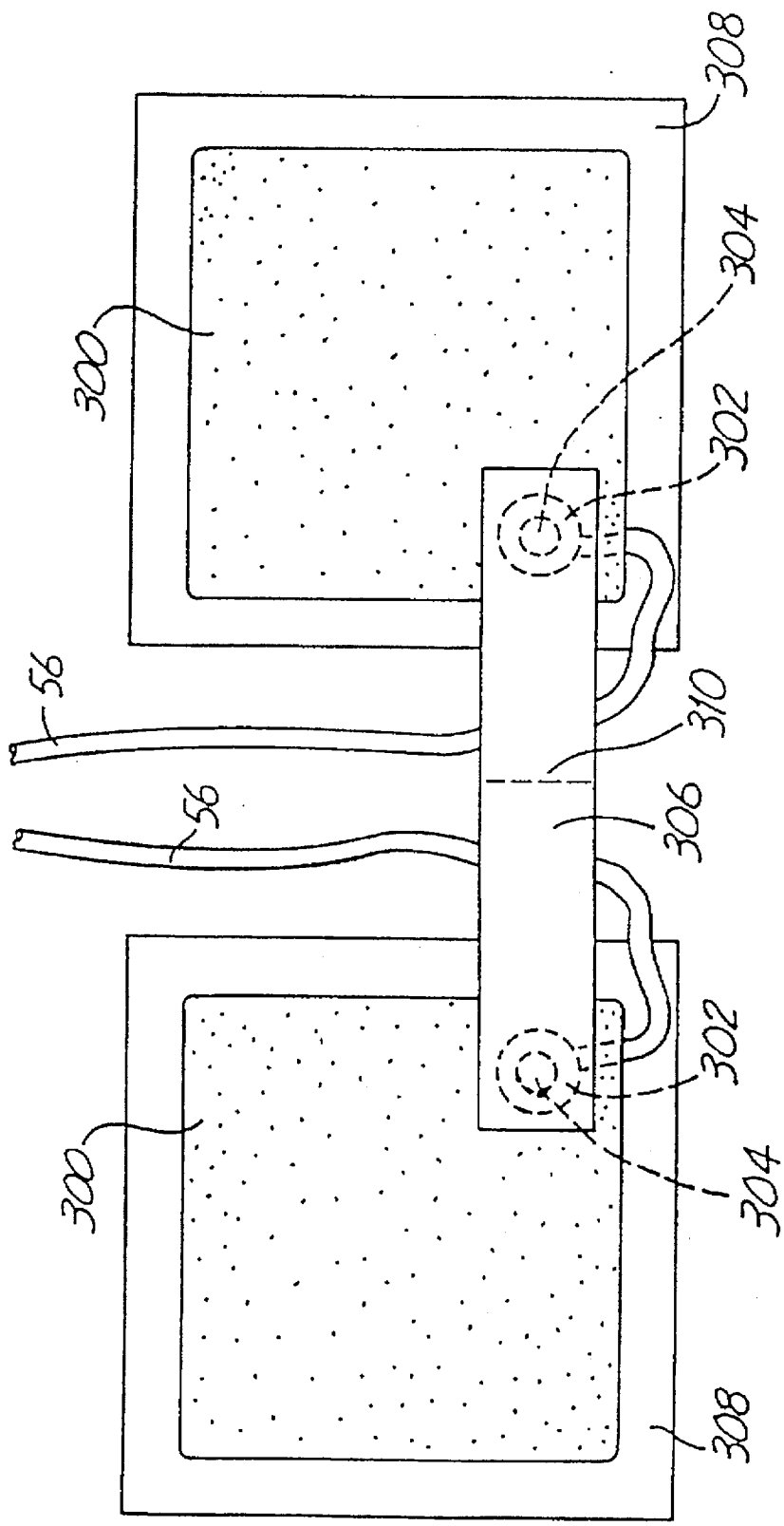
FIG. 6 is a detailed plan view of another embodiment of a pair of unpackaged electrodes.
Figure 7:
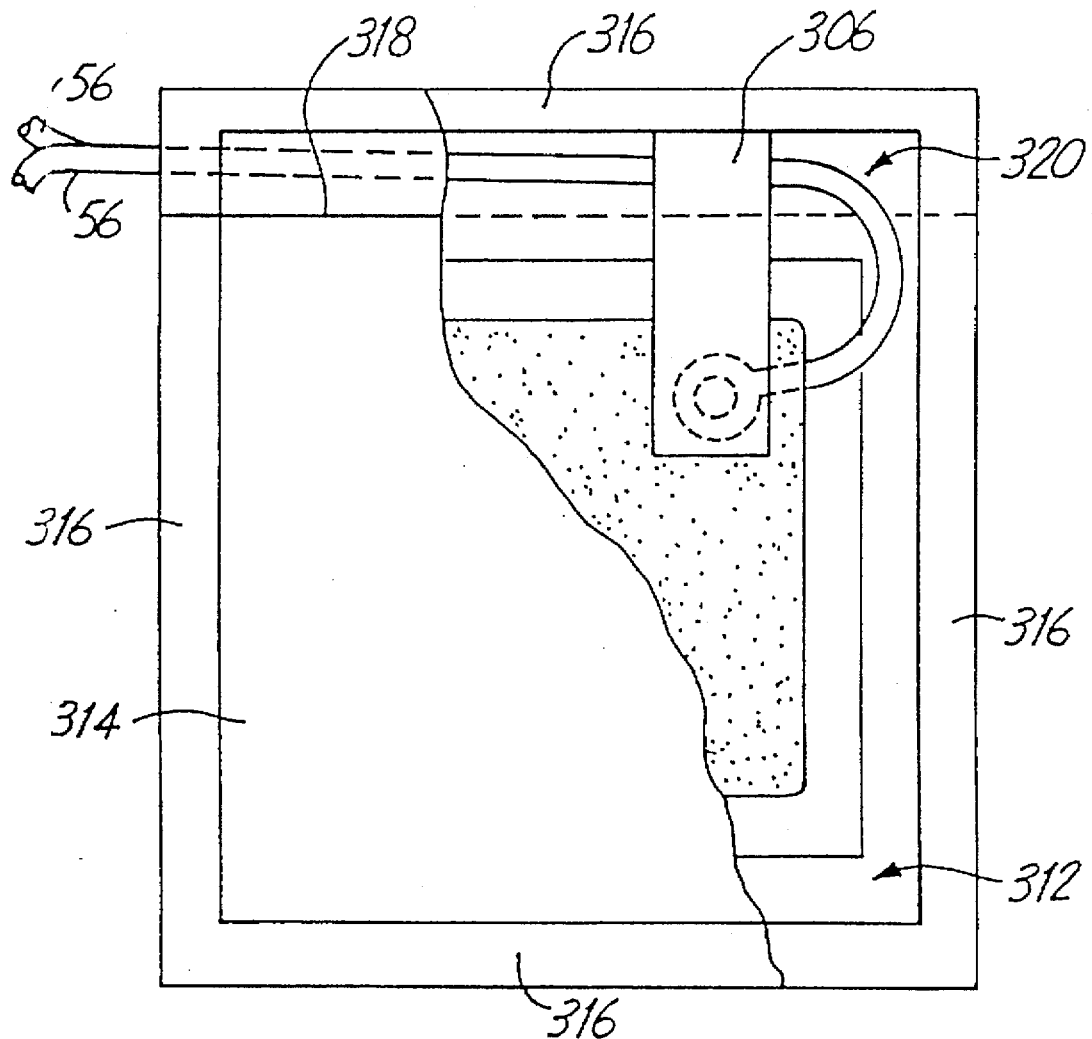
FIG. 7 is a plan view of the electrodes of FIG. 6 folded together and provided within a package shown partially broken away.

Yet another embodiment is illustrated in FIGS. 6 and 7. Electrodes 300 are provided which are similarly constructed as the aforementioned embodiments, including a backing layer, a conductive adhesive layer and a conductive sheet therebetween. Lead wires 56 are preferably connected with the conductive sheets between the backing layer and the conductive adhesive layer by terminals 302. Each terminal 302 also preferably provides a conductor 304 at the surface of the backing layer of each electrode 300. A pair of electrodes 300 are connected together by a conductive connector 306, specifically connected at each end to a conductor 304 of a terminal 302. Again, conventional connection means can be used, such as conductive adhesives, heat bonding, solder or the like. Conductive connector 306 may comprise a thin foil, a fine wire, or the like, but preferably comprises a thin foil. Each electrode 300 is also preferably provided on a separate liner 308. A fold line 310 substantially bisects the conductive connector 306 so that electrodes 300 can be folded back to back with liners 308 against one another. Conductive connector 306 completes an electrical circuit for connecting lead wires 56 by way of terminals 302 and conductors 304.

Electrodes 300 are positioned within an electrode receiving space 312 of package 314 which may be conventionally constructed with sealed edges 316. The interior of the package is divided by a tear line 318 into electrode receiving portion 312 and an interior portion 320.

In accordance with this embodiment, it is important that at least one of lead wires 56 be properly threaded within the package so as to exit package 314 at one of its edge seals 316 from within interior portion 320 of package 314. Moreover, conductive connector 306 forms a loop that extends within interior portion 320 of package 314. Preferably, both of lead wires 56 pass through the loop defined by conductive connector 306 when the electrodes are positioned back to back as folded along fold line 310. More particularly, lead wires 56 pass between conductive connector 306 and an edge of a liner 308. Furthermore, conductive connector 306 is sufficiently long so that when the electrodes are folded back to back, conductive connector 306 forms the loop so as to facilitate both lead wires 56 within interior portion 320. By this embodiment, package 314 can be easily opened along tear line 318 by a user grasping lead wires 56 where they exit package 314 at edge seal 316. Then, tearing the package open along tear line 318 will also tear or break conductive connector 306. Lead wires 56, in this case, act as a tear strip facilitating easy opening of package 314. This construction is advantageous in that in a single action opens the electrode package, breaks the electrical circuit, and removes the electrodes from the package. As above, the function of making and breaking the electrical circuit completed by connector 306 between lead wires 56 can be monitored, as set out below, for determining the presence of fresh electrodes 300.

As an alternative construction to each of the above-described embodiments, liners 61, 206 and 308 could instead comprise a single liner to which both electrodes 50, 200, and 300 respectively, are adhered. To do this, the liners would also be folded to position the electrodes within the respective packages. However, in order to provide that conductive connectors, 64, 208, and 306, respectively, extend across tear lines 69, 220 and 318, respectively, the conductive connectors must be of sufficiently greater length than the distance between the electrodes on the single liner so that when the single liners are folded, the conductive connectors will form a loop that extends sufficiently away from the folded edge of the single liner.

Figure 8:
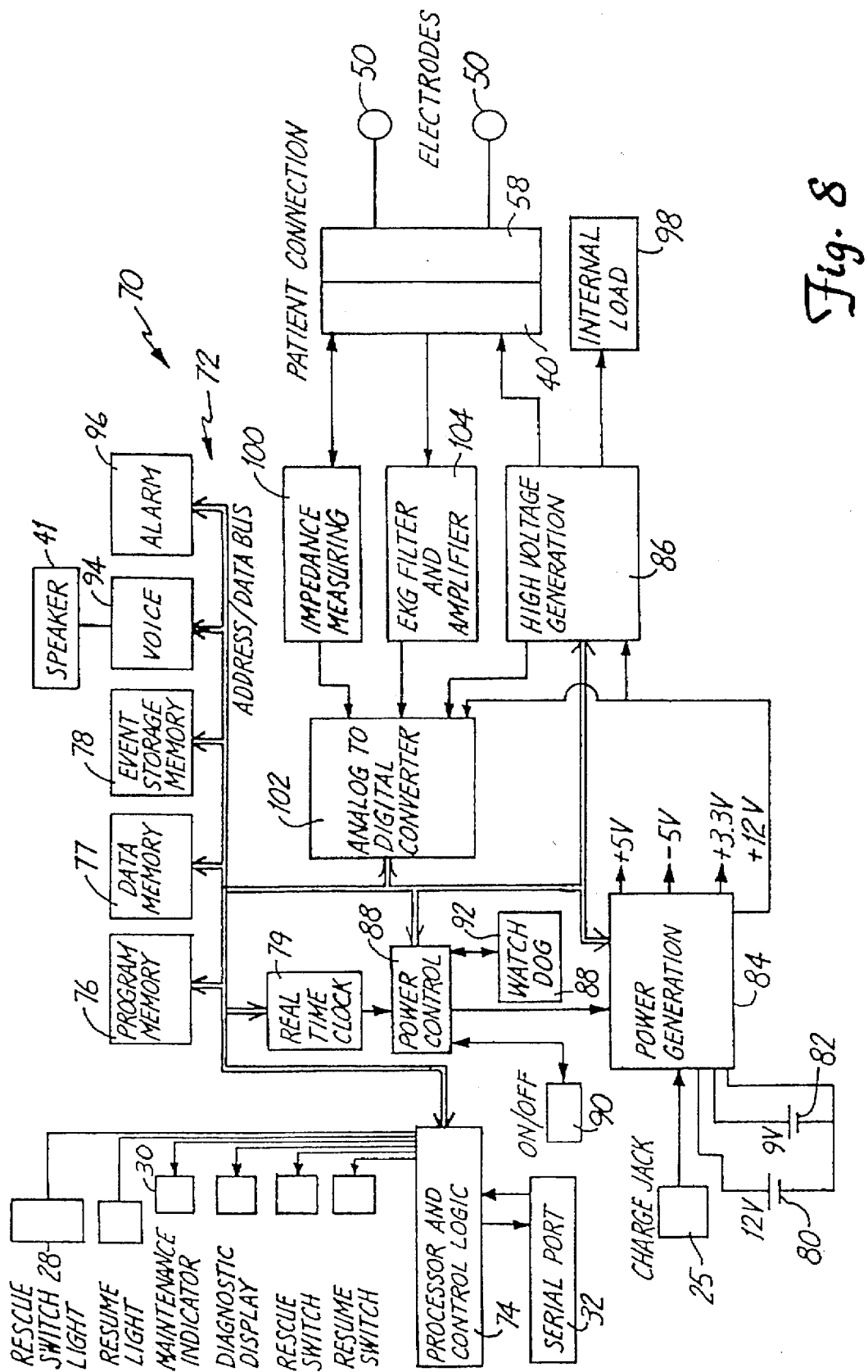
FIG. 8 is a block diagram of an electrical system of an AED.

FIG. 8 is a block diagram of electrical system 70 of defibrillator 10. The overall operation of defibrillator 10 is controlled by a digital microprocessor-based control system 72 which includes a processor 74 interfaced to program memory 76, data memory 77, event memory 78 and real time clock 79. The operating program executed by processor 74 is stored in program memory 76. Electrical power is provided by a rechargeable twelve volt lead-acid cartridge battery 80 and a nine volt battery 82 which are removably positioned within the battery compartment and connected to power generation circuit 84. Charging port 34 is coupled to power generation circuit 84, enabling twelve volt battery 80 to be connected to a twelve volt vehicle battery (not shown) or a 120 VAC charger (also not shown) and recharged while mounted within defibrillator 12. Alternatively, battery 80 can be removed from defibrillator 10 and charged in a stand-alone charger (not shown).

Power generation circuit 84 is also connected to power control circuit 88 and processor 74. Power control circuit 88 is connected to lid switch 90, watch dog timer 92, real time clock 79 and processor 74. Lid switch 90 is a magnetic read relay switch in one embodiment, and provides signals to processor 74 indicating whether lid 38 is open or closed. Data communication port 32 is coupled to processor 74 for two-way serial data transfer using an RS-232 protocol. Rescue switch 28, maintenance indicator 30, rescue switch light 29, resume switch 48, diagnostic display panel 37, voice circuit 94 and piezoelectric audible alarm 96 are also connected to processor 74. Voice circuit 94 is connected to speaker 41. In response to voice prompt control signals from processor 74, circuit 94 and speaker 41 generate audible voice prompts.

High voltage generation circuit 86 is also connected to and controlled by processor 74. Circuits such as 86 are generally known, and disclosed, for example, in the commonly assigned Persson et al. U.S. Pat. No. 5,405,361, which is hereby incorporated by reference. In response to charge control signals provided by processor 74, high voltage generation circuit 86 is operated in a charge mode during which one set of semiconductor switches (not separately shown) cause a plurality of capacitors (also not shown), to be charged in parallel to the 12 V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 40 which is connected to the high voltage generation circuit 86.

Impedance measuring circuit 100 is connected to electrode connector 40 and real time clock 79, and is interfaced to processor 74 through analog-to-digital (A/D) converter 102. Impedance measuring circuit 100 receives a clock signal having a predetermined magnitude from clock 79, and applies the signal to electrodes 50, for example, through connector 40. The magnitude of the clock signal received back from electrodes 50 through connector 40 is monitored by impedance measuring circuit 100. An impedance signal representative of the impedance present across electrode connector 40 is then generated by circuit 100 as a function of the ratio of the magnitudes of the applied and received clock signals (i.e., the attenuation of the applied signal). For example, if electrodes 50 within an unopened package 60 are connected by conductive connector 64 and connector 58 is properly connected to connector 40 on defibrillator 10, a relatively low resistance (e.g., less than about 10 ohms) should be present across connector 40. If package 60 is opened, connector 58 is not properly connected to connector 40, or the electrodes are not properly positioned on the patient, a relatively high resistance (e.g., greater than about two hundred and fifty ohms) will be present across connector 40. The resistance across connector 40 will be between about twenty and two hundred ohms when fresh electrodes 50 are properly positioned on the patient with good electrical contacts. The impedance signal representative of the impedance measured by circuit 100 is digitized by A/D converter 102 and provided to processor 74.

Figure 9:
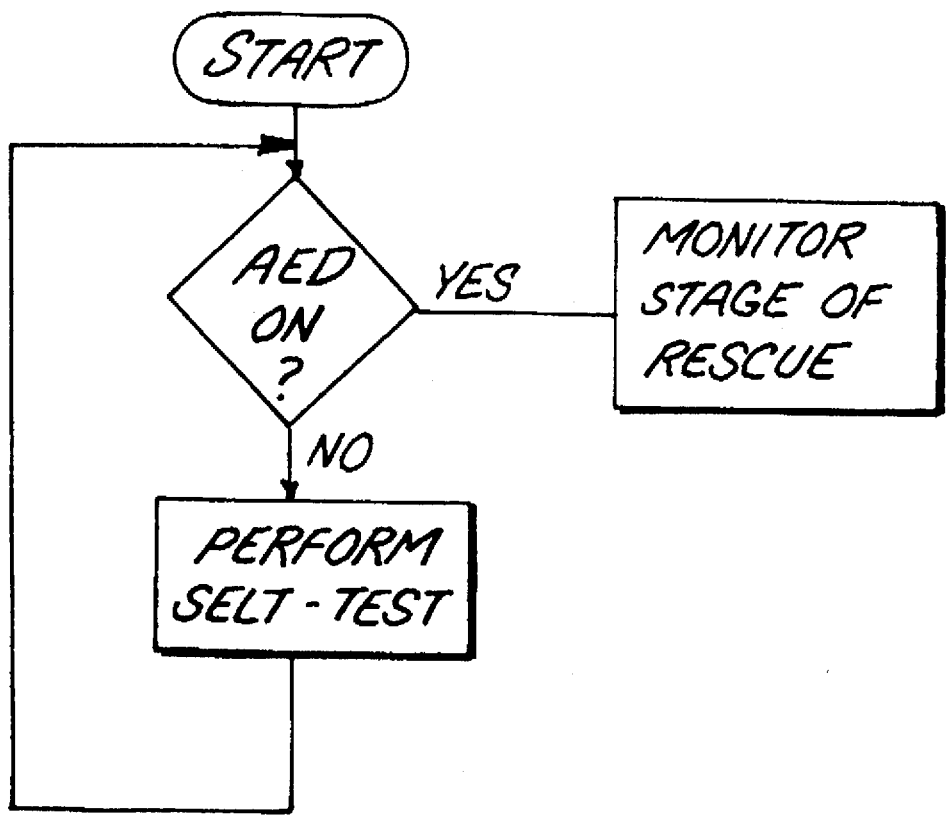
FIG. 9 is a flow diagram of a state monitoring procedure according to the present invention.

The present invention will be described with particular reference to AED 22 and electrodes 50 as described and illustrated above. AED 22 of the present invention is programmed to monitor for two basic states. The first state is when AED 22 is not being used for a rescue, and the second state is when AED 22 is being used for a rescue. In the first state, processor 74 initiates and performs a self-test which will then detect the presence of fresh electrodes 50, as described above. In the second state, when the AED is being used for a rescue, processor 74 monitors the rescue features. A sample flow chart of this is illustrated in FIG. 9.

In addition to monitoring the state of the AED, electrodes 50 of the present invention are coupled with detection means to determine a specific stage of a cardiac arrest rescue procedure. Specifically, AED 22 has the ability to determine which of at least five stages the AED is at during a rescue procedure. These stages include: 1) rescue initiated; 2) preparing victim; 3) applying electrodes; 4) AED in use; and 5) rescue completed.

By monitoring the stages of a rescue and the states of the AED, a dynamic characteristic is added to the static aspect of the AED. The ability to track the stages and states, allows the AED to perform comprehensive real-time, rescue checking as well as static self-checking. For example, one embodiment of the present invention is to use internal clock 79 to track how long each stage of a rescue procedure takes. This information is then stored in memory for future review and statistical analysis as to how to modify and improve rescue procedures to reduce the time spent in specific stages of a rescue, and/or to improve the manner in which the time is used. The time management aspect of the invention provides a means to assure the quality of a rescue. The more time saved during a rescue procedure (from the time of collapse to the time of the first attempt to defibrillate the victim) directly translates into more lives saved. In general, the likelihood of successful resuscitation drops ten percent for each additional minute that the victim is not revived.

The present invention also has an enhanced voice prompting feature to prompt operators more often. This is because the AED is able to track the stages of a rescue with some precision, thus it knows what has been done and what needs to be done next. Examples of voice prompts include: "please open electrode package", "please pull electrodes apart", "please place electrodes on patient", "do not touch patient, analyzing rhythm", and "press flashing button to deliver shock". Additionally, tracking the stages and states of an AED allows the AED the ability to know if the electrodes are reused. For example, the electrodes may not be solidly contacted to the patient at some time during a rescue. In that case, the device could include a prompt such as "please check electrodes".

The present invention has the impedance values that indicate what stage a rescue procedure is in stored in memory such that, if necessary a rescue procedure can be entered in the middle of any stage and the AED is able to identify the stage and proceed accordingly. This is beneficial because there may be times when a package of electrodes is bad, or an operator destroys a package of electrodes out of panic or for other reasons. If this happens, a rescue procedure can be suspended, a new package of electrodes obtained, and then the rescue resumed or a new rescue started. The AED recognizes this change and jumps back to the appropriate spot in the new rescue attempt. Additionally, it is possible that the AED is accidentally or purposely turned off. If the AED is turned back on within a predetermined time (for example 15–30 seconds) the AED can be programmed to continue on from where it left off.

In the first stage, it has been determined that a victim is in need, or it is believed that a victim is in need, of rescue. Therefore a rescue attempt is initiated. Lid 38 of AED 22 is opened, turning on the AED. At this point, the electrode package is still intact and the impedance reading across connector 40 should be less than about 10 ohms.

In the second stage, the rescue personnel are preparing the victim for defibrillation rescue. At this point AED 22 is on, and package 60 has been torn open along tear line 69. As described above, conductive connector 64 is thus torn, breaking the circuit between lead wires 56 within package 60. At this stage, electrodes 50 are still connected together via liner 61. The impedance measured at connector 40 should be greater than about two hundred and fifty ohms and less than about one thousand ohms at this point.

In the third stage, the rescue personnel have separated the electrodes for placement on the victim. With the electrodes separated, and prior to placing them on the patient, the impedance measured at connector 40 should be infinite or at least greater than 10 kilo ohms.

In the fourth stage, electrodes 50 are applied to the patient for rescue. The impedance measured at this point should be typically between about twenty five and two hundred ohms, depending on body size of victim, placement of electrodes on the victim and a multitude of other factors.

In the fifth stage, the rescue is complete, and electrodes 50 have been removed from the victim. At this point, the impedance should once again be measured at infinity or greater than 10 kilo ohms.

In an alternative embodiment of the present invention, the impedances measured by AED 22 at the different stages are changed. For example, if electrodes 50 within an unopened package 60 are connected by conductive connector 64 and connector 58 is properly connected to connector 40 on defibrillator 10, a low resistance (e.g., less than about 1 ohm) should be present across connector 40. If package 60 is opened and electrodes are not yet pulled apart, the resistance at connector 40 will be between about 2.5 and ten ohms. If package 60 is opened and the electrodes are pulled apart, a relatively high resistance (e.g., greater than about two hundred and fifty ohms) will be present across connector 32. The resistance across connector 40 will be between about twenty five and two hundred ohms when fresh electrodes 50 are properly positioned on the patient with good electrical contacts.

Figure 10:
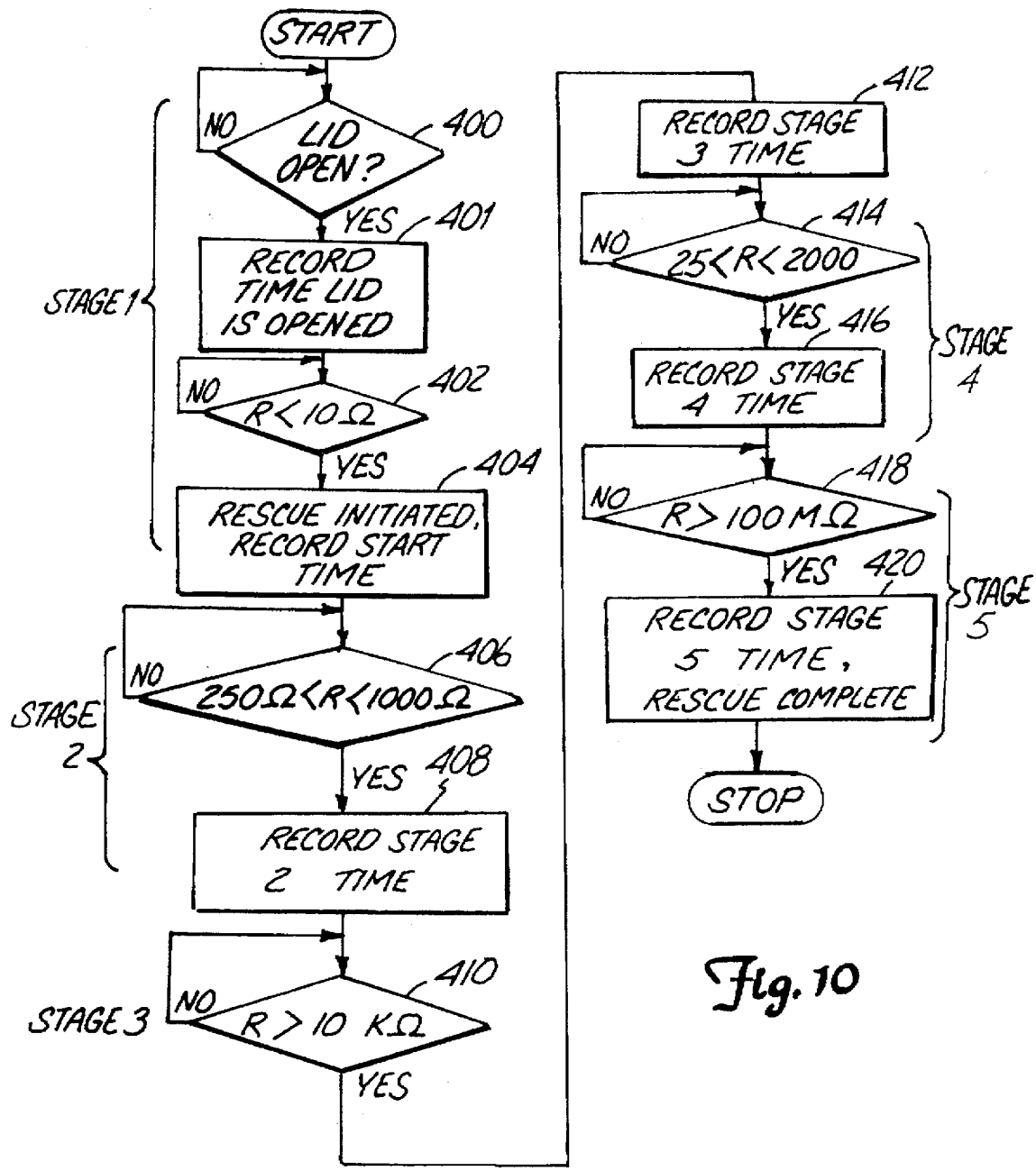
FIG. 10 is a flow diagram of a stage monitoring procedure according to the present invention.

A simplified logic flow chart of one embodiment of a stage monitoring procedure is illustrated in FIG. 10. Blocks 400, 401 and 402 verify that the AED is on and that the electronic package is still intact. The time of the rescue being initiated is then recorded in block 404. Block 406 verifies that the AED is now in stage two. Block 408 then records this time. Block 410 verifies that the electrodes are separated and not applied to the victim, and block 412 records this time. Blocks 414 and 416 verify that the electrodes have been placed on the victim and records the time. Finally, blocks 418 and 420 verify that the electrodes have been removed (rescue completed) and the time is recorded.

Although the present invention has been described with reference to preferred embodiments, those skilled in the art will recognized that changes can be made in form and detail without departing from the spirit and scope of the invention.

What is claimed is:

1. An automated external defibrillator (AED) having a packaged pair of electrodes electrically connected together, wherein the AED is capable of monitoring the state it is in, the AED comprising:

a case;

an electrode terminal mounted to the case;

a high voltage circuit contained in the case and electrically connected to the electrode terminal; and a control system coupled to the electrode terminal and the high voltage circuit wherein the control system includes state detection means for determining the state of the AED, said states being (1) the AED is being used for a rescue and (2) the AED is not being used for a rescue.

2. The AED of claim 1, the AED being capable of performing a cardiac arrest rescue procedure on a patient, the rescue procedure having a plurality of rescue stages, wherein the control system further comprises impedance monitoring means for monitoring the specific stages of a cardiac arrest rescue procedure.

3. The AED of claim 1, the AED being capable of performing a cardiac arrest rescue procedure on a patient, the rescue procedure having a plurality of rescue stages, wherein the control system further comprises rescue stage monitoring means for monitoring the specific stages of a cardiac arrest rescue procedure.

4. The AED of claim 3 wherein the packaged pair of electrodes comprises a package of flexible material defining a pouch having an interior cavity including first and second medical electrodes within an electrode receiving space of said interior cavity, each electrode comprising an electrically non-conductive flexible backing layer, a layer of electrically conductive adhesive disposed on said flexible backing layer and a lead wire extending therefrom and electrically connected with said conductive adhesive, wherein said first and second electrodes are each disposed on an electrically non-conductive liner, and an electrical connector is provided between said first and second electrodes for electrically completing a circuit connecting the lead wire of said first electrode to the lead wire of said second electrode.

5. The AED of claim 4, wherein the lead wires from said first and second electrodes extend through an opening provided through said package to the outside of said package.

6. The AED of claim 5, further including a tear line along which the package is to be opened and which divides the interior cavity of the package into said electrode receiving space and an interior portion.

7. The AED of claim 4 wherein the liners of the first and second electrodes have a plurality of holes formed therein.

8. An automated external defibrillator (AED) having a packaged pair of electrodes electrically connected together, wherein the AED is capable of monitoring the state it is in, the AED comprising:

a case;

an electrode terminal mounted to the case;

a high voltage circuit contained in the case and electrically connected to the electrode terminal; and a control system coupled to the electrode terminal and the high voltage circuit wherein the control system includes state detection means for determining the state of the AED and further includes rescue stage monitoring means for monitoring the stage of a rescue the packaged pair of electrodes having a package of flexible material defining a pouch having an interior cavity including first and second medical electrodes within an electrode receiving space of said interior cavity, the package including a tear line along which the package is to be opened and which divides the interior cavity of the package into said electrode receiving space and an interior portion, each electrode comprising an electrically non-conductive flexible backing layer, a layer of electrically conductive adhesive disposed on said flexible backing layer and a lead wire extending therefrom and electrically connected with said conductive adhesive, wherein said first and second electrodes are each disposed on an electrically non-conductive liner, and an electrical connector is provided between said first and second electrodes for electrically completing a circuit connecting the lead wire of said first electrode to the lead wire of said second electrode, the lead wires from said first and second electrodes extending through an opening provided through said package to the outside of said package.

9. The AED of claim 8 wherein said electrical connector comprises a flexible conductive strip, and said first and second electrodes are provided adjacent to one another in said package with their backing layers generally parallel to one another and with a loop formed in the electrical connector, said loop extending across said tear line and into said interior portion of said package from said electrodes within said electrode receiving space so that by opening the package along said tear line, the electrical connector can be broken, said first electrode being provided on a separate liner than the liner of said second electrode.

10. The AED of claim 8, wherein said electrical connector comprises a flexible conductive strip, and said first and second electrodes are provided adjacent to one another in said package with their backing layers generally parallel to one another and with a loop formed in the electrical connector, said loop extending across said tear line and into said interior portion of said package from said electrodes within said electrode receiving space so that by opening the package along said tear line, the electrical connector can be broken.

11. The AED of claim 10, further including a strip of tear resistant material connected to said electrical connector and positioned within said interior portion.

12. The AED of claim 11, wherein said strip of tear resistant material extends through an opening of said package to provide a gripping means to facilitate easy opening of said package.

13. The AED of claim 10, wherein said flexible conductive strip includes a portion extending transverse from said loop and which extends through an opening of said package to provide a gripping means to facilitate easy opening of said package.

14. The AED of claim 10, wherein at least one of said lead wires is disposed within said package through said loop and within said interior portion so as to pass through the material of said package from said interior portion.

15. The AED of claim 10, wherein said first electrode is provided on a separate liner than the liner of said second electrode.

16. The AED of claim 10, wherein the backing layers of said first and second electrodes each include a conductor portion, and said electrical connector is connected between the conductor portion of the backing layer of said first electrode and the conductor portion of the backing layer of said second electrode.

17. The AED of claim 16, wherein the lead wire of each electrode extends partially within the electrode between the backing layer and the conductive adhesive, and a terminal is provided to electrically connect the lead wire within the electrode to the conductor portion of the backing layer.

18. The AED of claim 8, wherein said electrical connector comprises a flexible conductive strip, and said first and second electrodes are provided adjacent to one another in said package with their backing layers generally parallel to one another and with a loop formed in the electrical connector, said loop extending across said tear line and into said interior portion of said package from said electrodes within said electrode receiving space so that by opening the package along said tear line, the electrical connector can be broken, at least one of said lead wires being disposed within said package through said loop and within said interior portion so as to pass through the material of said package from said interior portion.

19. An automated external defibrillator (AED) having a packaged pair of electrodes electrically connected together, the AED being capable of performing a cardiac arrest rescue procedure on a patient, the rescue procedure having a plurality, of rescue stages, the AED comprising:

a case;

an electrode terminal mounted to the case;

a high voltage circuit contained in the case and electrically connected to the electrode terminal; and a control system coupled to the electrode terminal and the high voltage circuit wherein the control system includes stage monitoring means for monitoring the specific stages of a cardiac arrest rescue procedure.

20. The AED of claim 19 wherein the control system further comprises state detection means for determining the state of the AED, said states being (1) the AED is being used for a rescue and (2) the AED is not being used for a rescue.

21. The AED of claim 20 wherein the packaged pair of electrodes comprises a package of flexible material defining a pouch having an interior cavity including first and second medical electrodes within an electrode receiving space of said interior cavity, each electrode comprising an electrically non-conductive flexible backing layer, a layer of electrically conductive adhesive disposed on said flexible backing layer and a lead wire extending therefrom and electrically connected with said conductive adhesive, wherein said first and second electrodes are each disposed on an electrically non-conductive liner, and an electrical connector is provided between said first and second electrodes for electrically completing a circuit connecting the lead wire of said first electrode to the lead wire of said second electrode.

22. The AED of claim 19 wherein the control system monitors at least the rescue stages of (1) rescue initiated, (2) preparing victim, (3) applying electrodes, (4) AED in use, and (5) rescue completed.

23. The AED of claim 22 wherein the rescue stages monitored correspond to sensed impedances as follows: (1) rescue initiated being less than about ten ohms, (2) preparing victim being greater than about two hundred-fifty ohms and less than about one thousand ohms, (3) applying electrodes being greater than ten kilo ohms, (4) AED in use being between about twenty-five ohms and two hundred ohms, and (5) rescue completed being greater than ten kilo ohms.

24. An automated external defibrillator (AED) having a packaged pair of electrodes electrically connected together, wherein the AED is capable of monitoring the state it is in, the AED comprising:

a case;

an electrode terminal mounted to the case;

a high voltage circuit contained in the case and electrically connected to the electrode terminal; and a control system coupled to the electrode terminal and the high voltage circuit wherein the control system includes an AED power on/AED power off detection portion.

25. The AED of claim 24 wherein the control system further comprises a rescue stage identifying and monitoring portion.

26. An automated external defibrillator (AED) having a packaged pair of electrodes electrically connected together, wherein the AED is capable of monitoring the state it is in, the AED comprising:

a case;

an electrode terminal mounted to the case;

a high voltage circuit contained in the case and electrically connected to the electrode terminal; and a control system coupled to the electrode terminal and the high voltage circuit wherein the control system includes a rescue stage identifying and monitoring portion and an AED power on/AED power off detection portion.

27. A method of monitoring the stage of a rescue procedure utilizing an automated external defibrillator (AED) having rescue stage monitoring means wherein the AED has a case, an electrode terminal mounted to the case, a high voltage circuit contained in the case and electrically connected to the electrode terminal, and a control system coupled to the electrode terminal and the high voltage circuit wherein the control system includes the stage monitoring means, and wherein the control system contains an internal clock and memory means, the method including the steps of:

(a) polling the AED to determine if the AED is on;

(b) using the internal clock to identify when the AED is turned on;

(c) storing in the memory means the time from the internal clock when the AED is turned on;

(d) measuring the resistance at the electrode terminal;

(e) determining a rescue stage from the measured resistance;

(f) identifying the time the rescue stage began with the internal clock; and (g) recording in the memory means the time of the rescue stage.

28. The method of claim 27 further including the step of:

(h) repeating steps (c) through (g) until the rescue is completed.

29. An automated external defibrillator (AED) having a packaged pair of electrodes electrically connected together, wherein the AED is capable of monitoring the state it is in, the AED comprising:

a case;

an electrode terminal mounted to the case;

a high voltage circuit contained in the case and electrically connected to the electrode terminal; and a control system coupled to the electrode terminal and the high voltage circuit wherein the control system includes an AED power on/AED power off detection portion and further includes a rescue stage identifying and monitoring portion.

30. An automated external defibrillator (AED) having a packaged pair of electrodes electrically connected together, the AED being capable of performing a cardiac arrest rescue procedure on a patient, the rescue procedure having a plurality of rescue stages, the AED comprising:

a case;

an electrode terminal mounted to the case;

a high voltage circuit contained in the case and electrically connected to the electrode terminal; and a control system coupled to the electrode terminal and the high voltage circuit wherein the control system includes impedance monitoring means for monitoring the specific stages of a cardiac arrest rescue procedure.

31. The AED of claim 30 wherein the control system further comprises state detection means for determining the state of the AED, said states being (1) the AED is being used for a rescue and (2) the AED is not being used for a rescue.

* * * * *

UNITED STATES PATENT AND TRADEMARK OFFICE
CERTIFICATE OF CORRECTION

PATENT NO. : 5,700,281
DATED : December 23, 1997
INVENTOR(S) : James E. Brewer, Kenneth F. Olson, John F. Stolte, Nora J. Utke, Gary B. Stendahl It is certified that error appears in the above-indentified patent and that said Letters Patent is hereby corrected as shown below:

Column 7, line 26, please change the word "dock" to the word "clock".

Column 7, line 47, please change "12 V" to "12V".

Column 9, line 25, please change the word "tom" to the word "torn".

Column 9, line 58, please change the words "connector 32" to the words "connector 40."

Signed and Sealed this

Twenty-first Day of April, 1998

Attest:

BRUCE LEHMAN

Attesting Officer

Commissioner of Patents and Trademarks